(12) United States Patent
Moffett et al.

(10) Patent No.: US 6,275,046 B1
(45) Date of Patent: Aug. 14, 2001

(54) COTTON MOISTURE METER

(75) Inventors: Steve Moffett, Lubbock; Paul Mohr, Wolfforth, both of TX (US)

(73) Assignee: Lubbock Electric Co., Lubbock, TX (US)

( * ) Notice: Subject to any disclaimer, the term of this patent is extended or adjusted under 35 U.S.C. 154(b) by 0 days.

(21) Appl. No.: 09/332,353

(22) Filed: Jun. 11, 1999

Related U.S. Application Data

(60) Provisional application No. 60/128,013, filed on Apr. 6, 1999.

(51) Int. Cl.[7] .......................... G01R 27/04; G01R 27/08; G01R 27/32; G01N 25/56

(52) U.S. Cl. .......................... 324/640; 324/695; 324/665; 324/632; 324/637; 324/639; 73/73

(58) Field of Search .......................... 324/664, 640, 324/695, 665, 637, 639, 632; 73/73

(56) References Cited

U.S. PATENT DOCUMENTS

| | | | |
|---|---|---|---|
| 2,659,860 | * 11/1953 | Breazeale | 324/640 |
| 3,644,826 | * 2/1972 | Cornetet, Jr. | 324/637 |
| 3,714,560 | * 1/1973 | Farr | 324/668 |
| 4,131,845 | * 12/1978 | Pakulis | 324/640 |
| 4,468,610 | * 8/1984 | Hanson | 324/665 |
| 5,514,973 | * 5/1996 | Byler et al. | 324/695 |
| 5,621,330 | * 4/1997 | Greenwald et al. | 324/640 |
| 5,624,729 | * 4/1997 | Cohen et al. | 428/90 |
| 5,845,529 | * 12/1998 | Moshe et al. | 73/73 |
| 5,995,895 | * 11/1999 | Watt et al. | 701/50 |

* cited by examiner

Primary Examiner—Glenn W. Brown
Assistant Examiner—Wasseem H. Hamdan
(74) Attorney, Agent, or Firm—Mark E. Scott; Wendell Coffee

(57) ABSTRACT

The method and structure of a moisture measuring device that creates an electric field and then determines a moisture content of a specimen based on the effect the moisture of the specimen has on the electric field.

10 Claims, 2 Drawing Sheets

COTTON MOISTURE METER

CROSS REFERENCE TO RELATED APPLICATION

Applicant filed a Provisional Application on this subject matter on Apr. 6, 1999, Ser. No. 60/128,013. Specific reference is made to that document, it is incorporated herein by reference, and the disclosure and drawings therein are a part of this document as if they were reproduced in full below.

BACKGROUND OF THE INVENTION

1. Field of the Invention

This invention relates to the non-invasive measurement of moisture content of various materials. Electronic technicians have ordinary skill in this art.

2. Description of the Related Art

The related art is replete with devices for the noninvasive measurement of moisture content by use of electromagnetic waves. Although each application varies in its exact method of operation, for the most part each of the related art devices has a radio or microwave frequency signal generator which feeds an antenna. This antenna acts to transmit an electromagnetic wave through the specimen whose moisture content is to be measured. Opposite to, or otherwise in receiving relationship to, the transmission antenna is a receiving antenna. Between the two antennas in operational relationship is a specimen space wherein the specimen to be measured is placed during the measurement procedure.

The principle of operation of the related art devices is simply that an electromagnetic wave propagates through the specimen in question. The receiving antenna receives the electromagnetic wave and calculates an amount or percentage of water in the specimen based on any of a number of characteristics of the electromagnetic wave including signal strength, polarization, attenuation or absorption of the electromagnetic wave, phase angle or scattering of the electromagnetic wave.

The antennae of the related art devices are usually horn type directional wave guides, placed as close as possible to the specimen, that direct the propagating electromagnetic wave through a small or at least a particular portion of the specimen measured. If the transmitting horn cannot direct the propagating wave across the entire specimen at one time, an accurate reading of the moisture content in the overall specimen requires an average across the specimen.

The typical frequencies of electromagnetic waves used in the related art devices are in the microwave or radio frequency ranges. Using these high frequency electromagnetic waves creates a host of problems like: complex electric circuitry to create the high frequency signal; high frequency current amplification systems; impedance matching systems; matched polarization transmission and receiving antennae; superheterodyne receiving circuitry; and all the shielding necessary in such high frequency circuits to prevent unwanted noise and cross talk.

The related art devices measure the moisture content of specimens such as gypsum board, baled material including cotton, cotton and other materials as they fall within a chute, and other fibrous substances. The term cotton includes lint cotton, that is cotton already ginned or removed from the seed, and seed cotton, which has the cotton fibers still attached to the cotton seed.

SUMMARY OF THE INVENTION

Progressive Contribution to the Art

This invention measures the moisture of a specimen by generating an electric field with an electric field creation unit and then detecting that specimen's effect on the electric field with an electric field detection unit. By creating and detecting the presence or strength of an electric field, rather than having to transmit and receive an electromagnetic wave, the hardware required is not as complicated as that for the electromagnetic wave devices. Additionally, the frequencies at which the device operates can be significantly lower than the related art devices.

Objects of this Invention

An object of this invention is to measure moisture content of a specimen.

An object of this invention is to measure the moisture content of a specimen by creation and detection of an electric field through the specimen.

An object of this invention is to detect the moisture content of a specimen by measuring a field intensity increase based on the specimen's concentration of an electric field because of its moisture content.

An object of this invention is to measure the moisture content of a specimen by detecting an absence of an electric field because the moisture of a specimen placed therein directs the electric field to a ground plate.

An object of this invention is to detect the moisture content of a specimen as the specimen falls from an upper level to a lower level past a field generation plate and field detection plate.

An object of this invention is to measure the moisture content of baled cotton by detecting an increase or decrease in the electric field associated with the presence of moisture within baled cotton.

An object of this invention is to detect the moisture content of loose cotton as it falls past a detection device by detecting the attenuation or concentration of the electric field as a function of the moisture content therein.

Further objects are to achieve the above with devices that are sturdy, compact, durable, lightweight, simple, safe, efficient, versatile, ecologically compatible, energy conserving, and reliable, yet inexpensive and easy to manufacture, install, operate, and maintain.

Other objects are to achieve the above with a method that is rapid, versatile, ecologically compatible, energy conserving, efficient, and inexpensive, and does not require highly skilled people to install, operate, and maintain.

The specific nature of the invention, as well as other objects, uses, and advantages thereof, will clearly appear from the following description and from the accompanying drawings, the different views of which are not necessarily scale drawings.

CATALOGUE OF ELEMENTS

Figure 1:
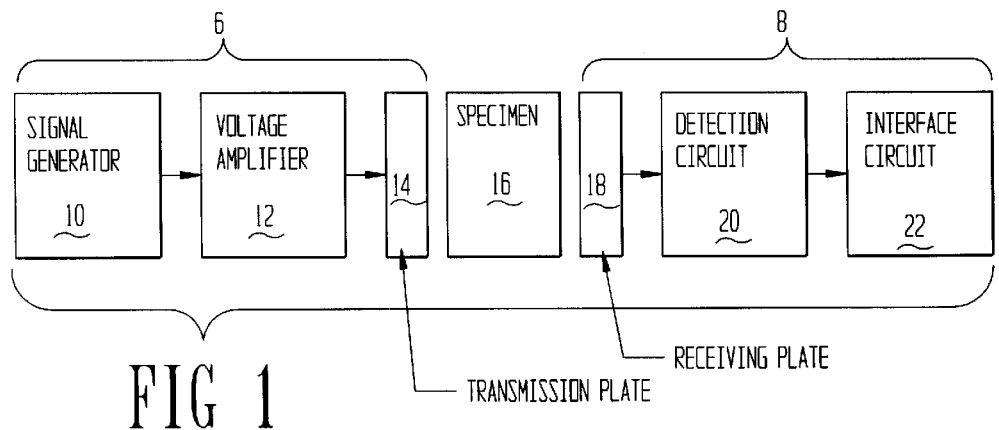
FIG. 1 is a block diagram representation of the invention.

As an aid to correlating the terms of the claims to the exemplary drawing(s), the following catalog of elements and steps is provided:
6 electric field generator
8 electric field detector
10 signal generator
12 voltage amplifier
14 transmission plate
16 specimen
18 receiving plate
20 detection circuit
22 interface circuit
24 ground plate
26 cotton bale
28 insulating material
30 conductive material
32 cotton
---- electric field lines
D plate separation
H1 transmission plate height
H2 receiving plate height
S1 transmission plate to specimen spacing
S2 receiving plate to specimen spacing

DESCRIPTION OF THE PREFERRED EMBODIMENTS

The electric field creation unit in the preferred embodiment is an electric field generator 6. The electric field detection unit of the preferred embodiment is an electric field detector 8. The electric field generator 6 and the electric field detector 8 comprise the two main components of the preferred embodiment.

The electric field generator 6 comprises a signal generator 10, a voltage amplifier 12, and a transmission plate 14. Signal generator 10 of the device is used to generate electrical signals at the desired frequency. Voltage amplifier 12, as the name implies, takes the signal from the signal generator 10 and amplifies the voltage to appropriate levels. Finally, the transmission plate 14, an electrically conductive element, is coupled to the voltage amplifier 12. The electric field is created around the transmission plate 14.

The electric field detector 8 comprises three elements. The first of the three elements is a receiving plate 18, an electrically conductive element. The receiving plate 18 is coupled to a detection circuit 20. This portion of the device detects the electric field created by the electric field generator 6 as modified by the presence and water content of a specimen 16. Finally, an interface circuit 22 couples to the detection circuit 20 and creates a standard output signal proportional to the water content of the specimen 16.

Figure 9:
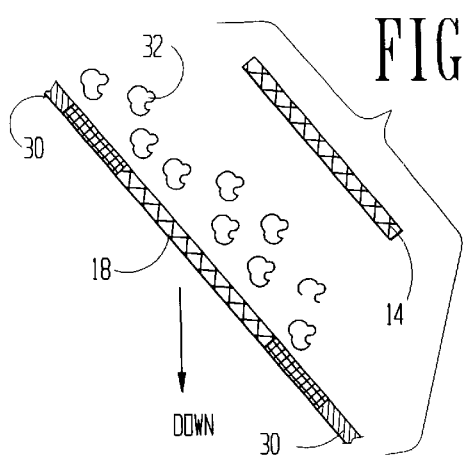
FIG. 9 shows an embodiment of the invention to detect the moisture content of cotton as it falls across a sloped surface.

The invention measures the moisture content of a specimen when the specimen is in a specimen space. Where the specimen is gathered or baled, as for instance a bale of cotton, the specimen space is roughly defined by the volume of the specimen. However, the invention works equally well for measuring the moisture content of a loose or ungathered specimen. An example might be cotton falling within a chute (FIG. 8) or cotton sliding down an inclined feed means (FIG. 9) to a gin stand in a cotton gin. The specimen space in this instance will be defined as a cross-sectional area of the flow of the loose or ungathered specimen cutting a swath of volume as it crosses between transmission plate 14 and the receiving plate 18. In either case, the volume created by the specimen between the two plates will be the specimen space.

The device of the generator 6 and the detector 8 measures the moisture content of the specimen by measuring the effect the specimen has on an electric field created by the device.

Figure 2:
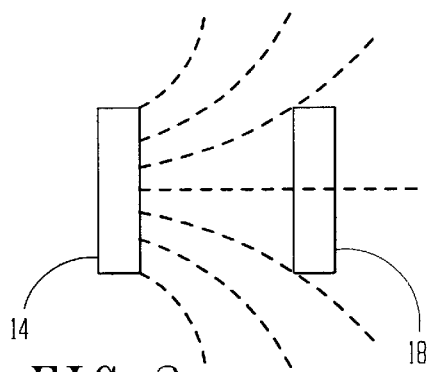
FIG. 2 is a representation showing the relationship of a transmission plate, electric field lines, and a receiving plate with no specimen present and in the absence of a ground plate.

Referring to FIG. 2, there are two electrically conductive plates labeled 14 and 18. For the purposes of explaining how the electric field is changed by the presence or absence of a specimen, it will be assumed in FIG. 2 that the two plates 14 and 18 are a significant distance from earth ground or any grounded conductor. If a voltage is applied to the transmission plate 14, an electric field is created thereby. As indicated by the dashed lines in FIG. 2, an electric field exists around the transmission plate 14. The dashed lines represent the electric field lines or the path of the flow of electric flux. The receiving plate 18 is not at ground potential and therefore the electric field is not affected by the presence of the plate 18.

Figure 4:
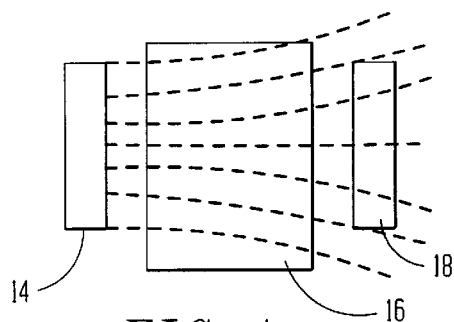
FIG. 4 shows the relationship of the transmission plate, the electric field lines, and the receiving plate when there is a specimen between the plates.

When a specimen 16 is placed between the transmission plate 14 and receiving plate 18, this placement affects electric field intensity. Referring to FIG. 4 there is a specimen 16 between the respective plates. The presence of the specimen 16 in this configuration tends to focus the electric field emanating from the transmission plate 14 toward the receiving plate 18 as shown. In this two plate configuration, the detection system looks for an increase of electric field as an indication of more moisture content of the specimen. As the moisture content of the specimen increases, the field focusing characteristic of the moisture laden specimen increases. The moisture content of the specimen is indicated by the voltage induced on the receiving plate 18 which is directly proportional to the moisture content of the specimen.

Figure 3:
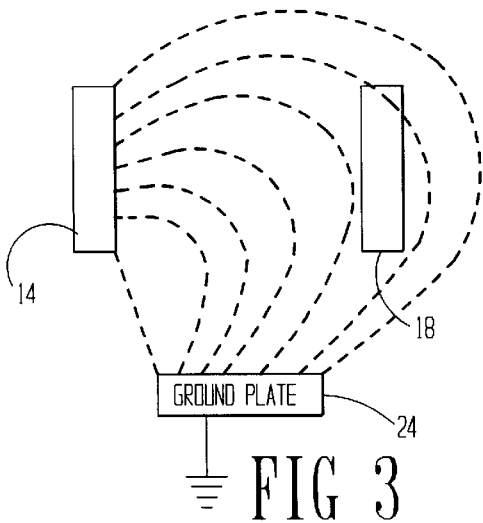
FIG. 3 shows the relationship of the transmission plate, the electric field lines, and the receiving plate when a ground plate is present.
Figure 5:
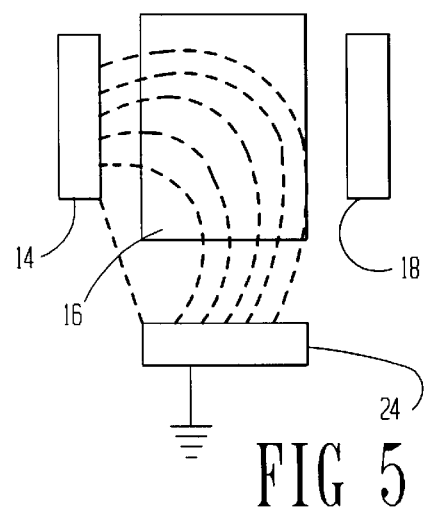
FIG. 5 shows the relationship of the transmission plate, the electric field lines, and the receiving plate when there is a specimen between the plates and there is present a ground plate.

Referring to FIG. 3 there is a second plate configuration embodiment. In this embodiment, in addition to the transmission and receiving plates 14 and 18 respectively, there is an additional ground plate 24, which is grounded, placed physically below plates 14 and 18. As seen in FIG. 3, the electric field is affected by the presence of the ground plate 24. In this configuration, the electric field, again indicated by dashed lines, varies between the transmission plate 14 and the ground plate 24. Referring to FIG. 5 there is indicated a specimen 16 placed in the three plate configuration. The presence of the specimen 16 in this configuration tends to focus the electric field toward the ground plate 24. The detection circuitry, in combination with the receiving plate 18, determines a moisture content of the specimen based on how much of the electric field is diverted to the ground plate by the moisture of the specimen. In this configuration the voltage induced on the receiving plate 18 will be inversely proportional to the moisture content of the specimen.

The above description of the characteristics of the electric field is somewhat idealized. Indeed, in FIG. 2 the electric field lines would propagate outward in all directions equally, but are shown in the figure only to exist between the two plates in the specimen space to simplify the drawing. Likewise, FIGS. 4 and 5 showing the presence of a specimen directing the electric field lines either to the receiving plate 18, as seen in FIG. 4, or to the ground plate 24, as seen in FIG. 5, are drawn assuming a perfect transmission of electric flux through the specimen 16 and ignore the electric field effect beyond the plates.

When the specimen 16 is cotton the electric field focusing characteristic of the moisture laden cotton does not result in a significant electric field change when the moisture content of the cotton exceeds 20 percent. Along these same lines, if a bale of cotton 26 being completely devoid of moisture content is placed between the transmission plate 14 and the receiving plate 18 of the configuration of FIG. 2, the electric field would be only slightly affected if at all by the presence of the cotton and therefore the electric field created by the transmission plate 14 would be substantially as indicated in FIG. 2. As the moisture content of the cotton 16 increases, the electric field strength at the receiving plate 18 increases proportionately. When the moisture content of the cotton bale 26 exceeds 20 percent, this represents a maximum field focusing effect and would create the situation as depicted in FIG. 4. Cotton is an example only of a possible specimen for use with this moisture measuring invention and is not intended to restrict the scope of the invention.

The description to this point has assumed a zero frequency voltage applied to the transmission plate 14. A unit working at zero frequency voltage may be operable in some locations where static electricity, and therefore static voltages and electric fields, are not a problem. However, if the invention is used in the presence of randomly fluctuating voltages created by static electricity, it would be desirable and advantageous for the voltage applied to the transmission plate 14 to be time varying at a particular frequency. The waveform of the voltage applied to the transmission plate 14 is contemplated to be substantially sinusoidal; however, the waveform of the applied voltage could be anything so long as the electric field detector 8 could discriminate the applied waveform from the random electric fields created by static electricity.

Although any frequency may be used for the time varying voltage applied to the transmission plate 14, it has been found hat in the use of the invention in cotton gins a frequency of 50 kHz works sufficiently well. However, the invention should not be construed to be limited to the use of 50 kHz since any frequency could be used. The use of 50 kHz was dictated by the frequency of noise generated in the particular application. The other noise generation devices included cathode ray tubes, switching power supplies, and specialty banding equipment used in many gins. It will be understood the descriptions of operation of the device using FIGS. 2–5 will not change except that the electric field detected will be that field varying at 50 kHz, or whatever frequency is chosen based on the particular application, and all other time varying electric fields induced on the receiving plate 18 are filtered out. Indeed, it would be possible that instead of using a particular frequency of electric field that the frequency of the electric field itself could change at a particular frequency. However, the electric circuitry required to implement such a complex frequency shifting operation would be substantially more than for a single frequency, but could still be an option for use in locations where significant ambient electric fields are present.

Figure 6:
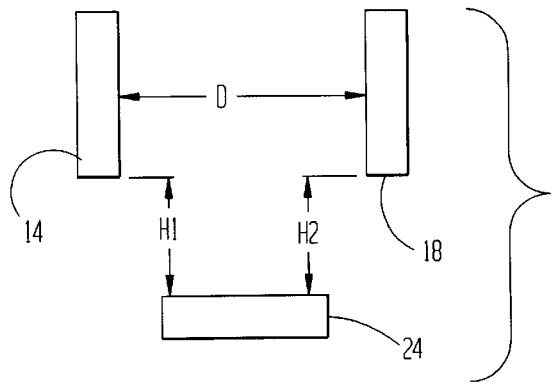
FIG. 6 is a not to scale view showing the physical relationships of the plates and ground plate.

Referring to FIG. 6 there is a representation of the physical placement of the transmission plate 14, receiving plate 18, and ground plate 24. It has been found in this invention that the separation distance of the transmission plate 14 and the receiving plate 18, represented as plate separation D, should be less than the sum of the transmission plate height H1 and the receiving plate height H2. The plate heights H1 and H2 are the difference of the level of the bottom of the plates 14 and 18 and the level of the top of the plate 24.

Figure 7:
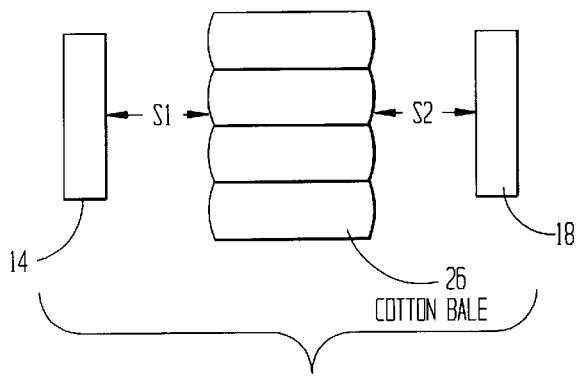
FIG. 7 indicates the relative spacing of the transmission and receiving plates in relationship to a cotton bale.

FIG. 7 shows a representation of a cotton bale 26 between the transmission plate 14 and the receiving plate 18. The transmission plate to specimen spacing S1 and the receiving plate to specimen spacing S2 need not be a small distance. That is, the plate spacings S1 and S2 could be as great as one foot away from the specimen 16 or the cotton bale 26 without adverse impact on the operation of the device. The spacing S1 and S2 could be greater than one foot, but such would require changes in the electrical circuitry.

The following is a description of the electrical circuitry used in this embodiment of the device. The electrical circuitry described is only one method of generating and detecting the electric field and as such should not be construed as limiting the breadth of the invention. Based on the frequencies used and the availability of electronic circuit components at the time of this application, the electrical circuit represents the best mode known to the inventor.

As previously mentioned, the frequency of the voltage applied to the transmission plate 14 in this embodiment is 50 kHz. This 50 kHz signal is created in the described embodiment using a 1 MHz clock signal divided sequentially by 2 and then by 10 by use of two integrated circuit components 4017 to get the desired frequency. The output of the second division unit is then fed to an FLT-U2 active filter component. This device is an off-the-shelf component that can, by the addition of external resistors, create a band pass filter at or in a range of desired frequencies. For this application, the desired center frequency of the band pass is 50 kHz. The output from the active filter is coupled to an operation amplifier TL082 set up to be a variable gain amplifier whose output is coupled to a voltage follower amplifier again made with a TL082. From this point the 50 kHz voltage signal crosses a capacitor and thereby moves from the signal generator 10 to the voltage amplification 12 portion of the device.

As the name implies, the voltage amplification 12 portion of the circuit takes the 50 kHz signal generated by the signal generator 10, increases the voltage, and applies that voltage to the transmission plate 14. Amplification in the described embodiment takes place by applying the 50 kHz signal to the gate of a power Metal Oxide Semi-Conductor Field Effect Transistor ("MOSFET") IRF 510. As is the function of a MOSFET, current is allowed to flow from the drain to the source relative to the voltage applied at the gate. In this configuration, the 50 kHz signal applied to the gate will create a near sinusoidal time varying current flow in the primary of a step up transformer. The time varying current flow in the primary of the transformer couples, by means of magnetic flux, to the secondary of the transformer. This coupling creates a voltage in the secondary of the transformer, which voltage is applied to the transmission plate 14.

The transformer of this embodiment is not an off-the-shelf product, but is rather a specially wound transformer for this application. Although its function is that of a step up transformer, the voltage gain across it may be higher than just the ratio of the primary to the secondary turns. The secondary of the transformer is wound with multiple secondary coils arranged such that the voltages induced on the secondary coils are added in series to get the secondary voltage. Additionally, it is possible also that the secondary circuit resonant frequency may be at or near the 50 kHz operating frequency and therefore the secondary output voltage may get a boost from a Tesla coil effect.

More specifically, the transformer is something of a specially wound autotransformer. The primary of the transformer comprises 50 turns of 26 gauge wire. This primary is wrapped around core material consisting of a ⅜" rod having a length of approximately 1½". The primary 50 turns is wrapped in one layer around the core material. The secondary is wrapped directly over the primary and consists of 500 to 700 turns of 26 gauge wire. The secondary is wrapped with the characteristic that after a complete layer of turns is applied, a single wire runs back to the top of the coil where the windings are again continued down and over the previous layer. In this embodiment, the magnetic circuit of the transformer, that is the core material of ⅜" rod, is not complete. By this it is meant that there is not a low reluctance magnetic flux path through rod material in a complete circuit. The magnetic flux of the transformer comprises the low reluctance path of the ⅜" rod material and a high reluctance air path around the windings themselves.

Summarizing the electric field generator of the overall electrical circuitry, the 1 MHz clock signal is sequentially divided by 2 and then 10 to result with a 50 kHz clock signal. This 50 kHz clock signal is applied to an active filter designed and constructed to be a band pass filter with a center frequency at 50 kHz. The output of the active filter is fed to a gain stage, this stage still within the signal generator 10, and then applied to a voltage amplifier 12 of the circuit where a current flow in the primary of the transformer induces voltages in secondary windings of the transformer. These voltages induced in the secondary windings are summed to get the secondary voltage which is applied to the transmission plate 14. It is the time varying voltage applied to the transmission plate 14 that creates a corresponding time varying electric field.

Detection and interpretation of the electric field is done within the electric field detector 8. The receiving plate 18, by being placed in the electric field generated around the transmission plate 14, will have an induced voltage. The voltage induced on the receiving plate 18 is fed to the detection circuit 20. The first element of the detection circuit 20 is a field effect transistor ("FET") operational amplifier TL084. The FET operational amplifier takes the relatively weak voltage signal induced on the receiving plate 18 and amplifies that signal for further processing. The output of the FET operational amplifier is coupled to a series of filters. Specific to the particular application in a cotton gin, the filters cut out any 60 Hz signal detected and specific frequencies associated with and created by the previously mentioned banding equipment. After passing these 2 filter stages, the signal is applied to an FLT-U2 active filter. The active filter is a band pass filter with a center frequency at 50 kHz.

There are many voltages created by static electricity in the operation of a cotton gin, or any of life's activities. The receiving plate 18 in combination with the FET operational amplifier will detect and create a signal for every electric field in the region of the receiving plate 18. However, the great majority of the electric fields created by operation of a cotton gin will not be time varying. That is, the electric fields generated by static electricity may vary in time, but this variance is only transitory. They will not vary at a particular frequency. To differentiate between electric fields created by static electricity and the electric field generated by this invention, the active filter FLT-U2 in the detection circuit 20 filters out all signals representing detected electric fields except for those signals created by electric fields varying at 50 kHz. The output of the second FLT-U2 represents only the electric field detected by the detection circuit 20 varying at 50 kHz. If the frequency of operation of the device is changed because of parameters of the particular application, the band pass filtering in this active filter will change to a center point of that frequency. The output of the active filter will be a signal whose peak voltage varies as a function of moisture content of the specimen being measured. The output of the active filter is fed to another gain stage made of a TL084 and then is fed to a diode 1N4148 where the signal is half-wave rectified. The remaining circuitry creates an output signal varying from 4 milli-amps to 20 milli-amps based on the peak voltage signal generated by the half-wave rectification through a diode. A 4 to 20 milli-amp signal is a standard interface signal that is compatible with many forms of control and monitoring equipment.

Best Mode and Operational Limits

There are many parameters of operation of this moisture measuring device that may be adjusted without undue adverse impact upon operation of the device. This section is to solidify what the inventor considers the best mode of operation of this moisture measuring device at the time of the filing of this application.

As previously mentioned, using the device to measure the moisture content of cotton in a cotton gin, the frequency of the best mode is 50 kHz. However, any frequency may be operational in the correct circumstances. To the best of our knowledge, there is no theoretical upper frequency limit at which the device is no longer operable. At present, only technical and economic limitations related to availability and price of components to create and detect the electric fields limit the potential upper range frequencies. Additionally, in the right circumstances even a zero frequency voltage could be applicable.

The specification speaks of electrically conductive elements and electrically conductive plates. As of the filing date of this invention the best mode is the use of matched transmission and receiving plates with each plate having a dimension of 6 inches by 9 inches. Other plate dimensions would work and the receiving and transmitting plate need not be the same size.

For ease of construction and to make a more aesthetically pleasing product, in this embodiment of the device the electric field generator 6 which includes the signal generator 10, voltage amplifier 12, and transmission plate 14 are all housed in a plastic box. That is, if one approached the device in operation one could not electrically contact the transmission plate 14 or any of the electrical circuitry of the electric field generator 6 as it would all be contained in a sealed electrical box. Likewise, the electric field detector 8 which includes the receiving plate 18, detector circuit 20, and interface circuit 22 are all contained in a near identical plastic box to that containing the electric field generator 6.

Placement of the transmission plate 14, receiving plate 18, and if present ground plate 24 are not particularly critical for correct operation of this device. For operation of the device without a ground plate 24, the transmission plate 14 and receiving plate 18 should be centered on the side of the specimen to which they are adjacent. Further, they should be on opposing sides of the specimen. For instance, if the specimen is a bale of cotton traveling down a conveyor, the best mode plate placement would be to place the transmission plate centered both in elevation with respect to the bale of cotton and centered with respect to length of the bale of cotton when the measurement is made. Further, the transmission plate 14 should be parallel to the side of the bale to which it is adjacent. Likewise, the receiving plate 18 will be centered with respect to elevation of the bale as well as the length of the bale, the plate will be parallel to the side of the bale to which it is adjacent, and further will be parallel to the transmission plate 14. It will be understood however that the invention is not limited to this exact placement with respect to the specimen being measured. Indeed the elevations of the transmission plate 14 and receiving plate 18 need not be the same nor does the placement with respect to the length of the specimen need be the same. It is an operable plate placement having the transmission plate 14 and receiving plate 18 on the same side of the specimen.

In configurations where a ground plate 24 is used the plate must satisfy the requirement that the distance of separation between the transmission plate 14 and the receiving plate 18 needs to be smaller than the sum of the heights H1 and H2. In the preferred embodiment the ground plate 24 lies in a plane which will be parallel to an adjacent face of the specimen to be measured. Further, the ground plate 24 will be centered between the transmission plate 14 and the receiving plate 18 and its plane will be at right angles to the planes of the receiving plate 18 and the transmission plate 14. It will be understood that the ground plate 24 need not be centered between the two plates and indeed the heights H1 and H2 need not be equal so long as the previously mentioned equation is satisfied. It is contemplated that the usual installation of the device will be to measure the moisture content of a bale of cotton as that cotton rests upon a scale made mostly of metallic material. Indeed, such a scale would act as the ground plate 24. In this configuration, the transmission plate 14 and the receiving plate 18 would be centered with respect to the length of the bale, but to satisfy the above equation the plates would be placed at or near an upper surface of the bale as it rests upon the scale.

As for the particular circuitry of the preferred embodiment, the specification has included many part numbers for the operational amplifiers, MOSFETs, and active filters used. Based on the frequency of use in a cotton gin, these devices represent the best mode known to the inventor. For operation in this particular application, a voltage of approximately 400 volts peak was created by the combination of the power MOSFET and specially wound transformer such that the peak voltage applied to the transmission plate 14 is 400 volts. The waveform of the voltage applied to the transmission plate 14 oscillates around zero volts and therefore the highest positive voltage applied to the transmission plate 14 is 400 volts and the most negative voltage applied to the transmission plate 14 is −400 volts. However, the invention is not limited to applying a sinusoidal voltage with no offset to the transmission plate 14. Indeed, it maybe possible to add sufficient direct current bias to the applied voltage such that only a time varying positive voltage would be applied to the transmission plate 14. Likewise, a negative direct current bias could be added such that only negative voltages could be applied to the transmission plate 14 and all of such would still be within the contemplation of this device.

In the application of measuring the moisture content of a cotton bale, the preferred use is to leave electric field generator 6 portion of the device operational at all times. Further, as a bale of cotton moves down a conveyor, it is contemplated that the best mode is to stop the bale of cotton such that the transmission plate 14 and the receiving plate 18 are centered as previously described so that a measurement may be taken. However, it is within the contemplation of this device that the moisture content of the bale of cotton could be done as it moves down conveying means without stopping for the moisture measurement.

In the best mode operation of the device the transmission plate 14 and the receiving plate 18 should be at least 6" away from the specimen being measured, for instance a bale of cotton. Further, the transmission plate 14 and the receiving plate 18 should be no more than 12" away from the specimen being measured, again for instance a bale of cotton. At plate to specimen separations greater than 12" the device may still be operational, but such will require modification to the electrical circuits. It has been found that the device is not operational when the transmission plate to specimen separation is less than approximately 4".

Operation of the device is relatively simple. In the application where the moisture content of a bale of cotton is determined, the electric field generator 6 is placed on one side of a path of travel of the cotton bale. This path of travel of a cotton bale is usually along a conveyor of some sort leading away from the cotton gin's baling equipment. On a second side in operation relationship to the electric field generator 6 will be placed the electric field detector 8. In this configuration, the conveying means will move the bale of cotton to be between the electric field generator 6 and the electric field detector 8. When the bale of cotton is in this position the electric field created by the electric field generator 6 will permeate the cotton bale 26 and the electric field detector 8 will measure the effect the moisture of the cotton bale 26 has on the electric field.

In the situation where the moisture measuring device is measuring a bale of cotton, the current state-of-the-art in making cotton bales is to hold the bale together with metallic bands. In some circumstances, after the bale is bound together with the metallic bands, a plastic cover is placed over the bale and bands. In applications where this is done, there is little chance that the metallic bands binding the cotton together may become grounded. However, it is contemplated that some applications of the device may be in situations where the metallic bands are exposed on the outer surface of the cotton bale and therefore there is at least the possibility that the bands themselves may become grounded as they move down a conveyor of metallic rollers. The possibility of a band becoming grounded is usually slight since the spacing of the rollers on a conveyor are different than the spacing of the bands on a bale which, in combination with the bunching effect created by the bands, make it unlikely that a band will drop far enough to contact a grounded metallic roller of a conveyor. Other conveying systems may be rubber belts which further lessen the possibility of grounding a metallic band. The bands themselves in their ungrounded state have little if any effect on the operation of the moisture measuring device. If by chance one of the bands becomes grounded, such grounded band will affect the moisture measuring capability of the device, but this effect is not substantial.

Figure 8:
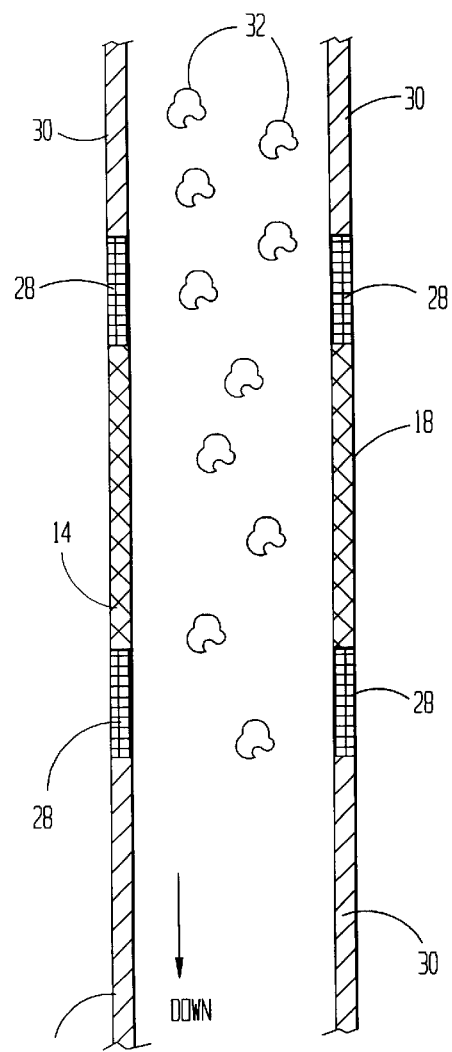
FIG. 8 shows an embodiment of the invention used to detect the moisture content of falling cotton as in a chute.

A second application of the moisture measuring characteristics of this device is shown in FIG. 8. In this figure, cotton 32 falls within a chute bounded by electrically conductive material 30. Disposed within the walls of the chute will be the transmission plate 14 and the receiving plate 18. So that electric fields may be generated and detected, the transmission plate 14 and receiving plate 18 must be electrically isolated from the conductive material 30 and such is done by presence of insulating material 28. Operation of the moisture measuring device in this configuration is very similar to the two plate configuration with the conveying means between them. In this case, the transmission plate 14 creates an electric field existing at least within the specimen space bounded by the conductive material 30. The receiving plate 18 has a voltage induced upon it proportional to the electric field produced. As the moisture laden cotton 32 falls within the chute bounded by the conductive material 30, the moisture of the cotton 32 affects the electric field produced by the transmission plate 14. The electric field detector 8 then determines a moisture content of the cotton 32 as previously described and produces an output signal for use by other gin machinery.

This document does not intend to distinguish between components that differ in name, but not in function. In the proceeding discussion, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct electrical connection or an indirect electrical connection via other devices and connections.

It must be understood that the theory of operation of the device as previously described is based on the theory of electric fields, the theory of electric field lines, and the flow of electric flux. This is only a theory explaining the characteristics of an electric field and should not be construed as a limitation on operation of the device. It is possible to completely explain operation of this electric field device by means of the cumulative effect of the electric di-pole of water in the specimen being measured, yet the electronics, plate placement and tuning would remain exactly the same. Stated a different way, the device should not be construed to be limited in the creation of electric field lines through the specimen to be measured or the flow of electric flux from the transmission plate to a surrounding ground or ground plate. It is the same invention to say that an electric field is created on a transmission plate 14 which tends to align the electric di-poles of the water in the specimen and it is the alignment of the di-poles in a particular direction that creates an electric field emanating from the specimen on its far side because of this alignment.

By the above specifications and drawings, one with ordinary skill in the art will understand how to make and use the invention as described. At this time the description above includes the best mode known to the inventor of carrying out his invention.

The embodiment shown and described above is only exemplary. I do not claim to have invented all the parts, elements or steps described. Various modifications can be made in the construction, material, arrangement, and operation, and still be within the scope of my invention. For example, this specification has used the term conductive plate to be both the transmission plate 14 and receiving plate 18. It is within the contemplation of this invention that rather than using plates as the charged element to create the electric field or a conductive element to detect the electric field that instead a wire mesh could be used. Likewise, given the right circumstances even a single strand of wire could be used to create the electric field and such would still be within the contemplation of this invention. Indeed, any conductive element to which a charge could be applied to create an electric field could be substituted for the conductive plates.

The restrictive description and drawings of the specific examples above do not point out what an infringement of this patent would be, but are to enable one skilled in the art to make and use the invention. The limits of the invention and the bounds of the patent protection are measured by and defined in the following claims.

I claim as my invention:

1. A structure of a moisture measuring device comprising:
   a) a specimen where the specimen's volume defines a specimen space,
   b) an electric field creation unit,
   c) an electric field created by said electric field creation unit throughout said specimen space,
   d) said electric field creation unit having,
      i) a signal generator creating a time varying voltage having a frequency, and
      ii) a first electrically conductive element adjacent to a boundary of the specimen space coupled to the signal generator to which the voltage is applied to create an electric field,
   e) an electric field detection unit adjacent to a boundary of said specimen space, wherein said electric field detection unit measures the electric field where the specimen is in the specimen space, the detection unit comprising,
      i) a second electrically conductive element disposed within the electric field that has a voltage induced upon it proportional to strength of the electric field, and
      ii) a detection circuit coupled to the electrically conductive element for detecting the induced voltage of a particular frequency,
   f) a third electrically conductive element substantially at ground potential disposed within the electric field, and
   g) said electric field detection unit detecting the induced voltage inversely proportional to the moisture content of the specimen.

2. The structure as defined in claim 1 wherein the frequency of the time varying voltage is approximately 50,000 cycles per second.

3. The structure as defined in claim 1 further comprising said first electrically conductive element being a conductive plate placed between six inches and twelve inches from the specimen.

4. The structure as defined in claim 1 further comprising said detected induced voltage frequency being approximately 50,000 cycles per second.

5. The structure as defined in claim 1 further comprising said second electrically conductive element being an electrically conductive plate placed twelve or fewer inches from the specimen.

6. The structure as defined in claim 1 further comprising an interface circuit that produces an output signal in a range of 4–20 milli-amps direct current.

7. The structure as defined in claim 1 further comprising:
   e) the first electrically conductive element being an electrically conductive plate having an axis through its center and normal to its major surface adjacent to a first boundary of the specimen space,
   f) the second electrically conductive element being an electrically conductive plate having an axis through its center and normal to its major surface adjacent to a second boundary opposite the first boundary and said second plate substantially parallel with and coaxial to the first electrically conductive plate.

8. The structure as defined in claim 1 further comprising:
   e) the first electrically conductive element being a first electrically conductive plate adjacent to a first boundary of the specimen space,
   f) the second electrically conductive element being an electrically conductive plate adjacent to a second boundary substantially at right angles to said first electrically conductive plate.

9. The structure as defined in claim 1 further comprising:
   e) said specimen is ungathered material falling along a path of travel,
   f) said second electrically conductive element disposed within a lower boundary of said specimen space, and
   g) said first electrically conductive element disposed on an upper boundary of said specimen space.

10. A structure of a moisture measuring device comprising:
- a) a specimen where the specimen's volume defines a specimen space,
- b) an electric field creation unit adjacent to a boundary of said specimen space,
- c) an electric field created by said electric field creation unit throughout said specimen space,
- d) an electric field detection unit adjacent to a boundary of said specimen space, wherein said electric field detection unit measures the electric field when the specimen is in the specimen space,
- e) said electric field creation unit is an electric field generator having,
  - i) a signal generator creating a time varying voltage having a frequency,
  - ii) a first electrically conductive element adjacent to the first boundary of the specimen space coupled to the signal generator to which the time varying voltage is applied to create the electric field,
- f) said electric field detection unit is an electric field detector having,
  - i) a second electrically conductive element adjacent to the second boundary of the specimen space within the electric field that has a voltage induced upon it proportional to strength of the electric field,
  - ii) a detection circuit coupled to the second electrically conductive element for detecting the induced voltages of a particular frequency, and
  - iii) an interface circuit coupled to the detection circuit which produces an output signal related to a moisture content of a specimen within the specimen space,
- g) a third electrically conductive element at ground potential, adjacent to a third boundary of the specimen space, and
- h) said detection circuit detecting the induced voltage inversely proportional to the moisture content of the specimen.

* * * * *